United States Patent
Bourdillon et al.

(10) Patent No.: US 11,969,379 B2
(45) Date of Patent: Apr. 30, 2024

(54) FREEZABLE PAD FOR PAIN RELIEF

(71) Applicant: LANSINOH LABORATORIES, INC., Alexandria, VA (US)

(72) Inventors: Katherine Anne Bourdillon, Leeds (GB); David Tom McCausland, Leeds (GB); Rush Bartlett, Austin, TX (US)

(73) Assignee: Lansinoh Laboratories, Inc., Alexandria, VA (US)

( * ) Notice: Subject to any disclaimer, the term of this patent is extended or adjusted under 35 U.S.C. 154(b) by 710 days.

(21) Appl. No.: 17/018,025

(22) Filed: Sep. 11, 2020

(65) Prior Publication Data
US 2021/0077295 A1 Mar. 18, 2021

Related U.S. Application Data

(60) Provisional application No. 63/049,227, filed on Jul. 8, 2020, provisional application No. 63/002,744, filed on Mar. 31, 2020, provisional application No. 62/899,389, filed on Sep. 12, 2019.

(51) Int. Cl.
*A61F 7/02* (2006.01)
*A61F 7/00* (2006.01)

(52) U.S. Cl.
CPC ...... *A61F 7/0241* (2013.01); *A61F 2007/005* (2013.01); *A61F 2007/0212* (2013.01); *A61F 2007/0219* (2013.01); *A61F 2007/0295* (2013.01)

(58) Field of Classification Search
CPC .............. A61F 13/00063; A61F 13/148; A61F 2007/005; A61F 2007/0212; A61F 2007/0219; A61F 2007/0295; A61F 7/0241
See application file for complete search history.

(56) References Cited

U.S. PATENT DOCUMENTS

| | | | |
|---|---|---|---|
| 6,579,543 B1* | 6/2003 | McClung | A61K 8/9761 424/734 |
| 2009/0204089 A1* | 8/2009 | Caldwell | A61K 36/185 604/385.02 |
| 2009/0312684 A1 | 12/2009 | Leonard et al. | |
| 2011/0052664 A1* | 3/2011 | Tennican | A61K 9/7007 604/304 |
| 2011/0184328 A1 | 7/2011 | Chieze et al. | |
| 2020/0085614 A1* | 3/2020 | Campbell | A61F 13/84 |

FOREIGN PATENT DOCUMENTS

WO 2010038231 A1 4/2010

OTHER PUBLICATIONS

International Search Report and Written Opinion for PCT/US2020/050476, mailed Nov. 18, 2020, 11 pages.

\* cited by examiner

*Primary Examiner* — Tigist S Demie
(74) *Attorney, Agent, or Firm* — Merchant & Gould P.C.

(57) ABSTRACT

A pad for treating a perineal area of a woman before or after childbirth includes a foam layer and a substance integrated with the foam layer. The foam layer is flexible, so that it can conform to the perineal area of the woman. The pad may optionally include a skin contact layer made of an impermeable material. The foam layer and/or the optional skin contact layer may include openings, such as perforations or slits. A method of using the pad may involve placing the pad in the perineal area before or after childbirth. The pad may be frozen, cooled or heated before use, in different embodiments.

30 Claims, 7 Drawing Sheets

FREEZABLE PAD FOR PAIN RELIEF

CROSS-REFERENCE TO RELATED APPLICATIONS

This application claims the benefit of U.S. Provisional Patent Application Nos. 62/899,389, filed Sep. 12, 2019; 63/002,744, filed Mar. 31, 2020; and 63/049,227, filed Jul. 8, 2020, all of which are entitled, "Freezable Pad for Pain Relief," and all of which are hereby incorporated by reference in their entireties into the present application.

BACKGROUND

Childbirth can cause a woman to experience any of a number of different changes to the perineal area (i.e., the region between the posterior vulva junction and the anus). Some of these changes are expected and relatively painless, such as bruising, stretching and swelling. In other cases, however, delivery can cause a vaginal tear and/or require an episiotomy (i.e., a surgical cut made at the opening of the vagina), which often require stitching and are associated with pain and discomfort as they heal in the days and weeks following birth.

Cold therapy, in the form of ice application, cryotherapy, and the like, is one accepted treatment for postpartum perineal pain and discomfort. Cold therapy works by reducing blood flow to the perineal area, which can significantly reduce inflammation and swelling that causes pain. Cold therapy can also temporarily reduce nerve activity, which may help relieve pain. Direct contact between a very cold substrate and the skin, however, can damage the skin, sometimes quite severely.

Herbal solutions are also sometimes used to provide relief to injured perineal tissue, through astringent or anti-inflammatory properties. Some herbal ingredients, however, can irritate and/or sensitize the skin at higher concentrations or when applied incorrectly.

Another treatment for postpartum perineal pain is oral pain medications. These medications are not specifically directed to the perineal area, however, and have all the known side effects of oral pain medications.

Therefore, there remains a need for an improved treatment for postpartum perineal pain and discomfort. Ideally, such a treatment would be easy to use, relatively long lasting, and free from side effects, such as damage to, or irritation of, the skin. At least some of these objectives will be addressed by this disclosure.

SUMMARY

This disclosure describes a freezable pad for relief of postpartum perineal pain and discomfort. The pad generally includes layer of a foam material and a substance (or multiple substances) integrated with the foam layer. The foam layer may be made of an open cell foam material and may be at least partially permeable. The foam layer may also include one or more openings that extend through the thickness of the foam, such as but not limited to perforations or slits. In some embodiments, the perineal pad may include a skin contact layer, which may be impermeable or at least less permeable than the foam layer. The foam layer is impregnated, coated, soaked, or otherwise configured to contain at least one therapeutic substance, which may be in the form of a liquid, a viscous substance, a semi-liquid, a gel, a solution, or the like. The therapeutic substance may contain one or more active pharmaceutical ingredients and/or herbal substances within a solution. The therapeutic substance may reside within, be a part of, be adhered to, or be wicked by the substrate. In various embodiments, the pad may be applied to the skin of a woman's perineal area at different temperatures, for example heated, body temperature, room temperature, chilled/cold, or frozen. The temperature of the pad may often add to the therapeutic effects, relieving pain and/or discomfort.

In one embodiment, the pad has a two-layer (or "bilayer") configuration, in which the skin contact layer is non-absorbent. This layer protects the skin from direct contact with foam substrate layer, which holds or otherwise contains the therapeutic substance(s). In some embodiments, the skin contact layer may still be made of a non-absorbent material but may include perforations, slits, holes, unsealed areas, channels or the like, to allow a limited amount of the substance(s) in the foam layer to pass through the skin contact layer to contact the woman's skin. In such embodiments, the substance(s) may have an added therapeutic effect due to the skin contact.

According to one aspect of the disclosure, the freezable pad includes an absorbent foam layer, laminated or bonded to a skin-facing, non-absorbent layer. The skin-facing layer may be perforated or slit. The foam layer may also be perforated or slit. The presence of perforations and/or slits may facilitate movement of non-medicated fluid, gel, gasifying substance, semi-liquid foam, thermal gradient and/or medicated substance between the pad and the perineal area or other body area being treated. In some embodiments, sections of the foam are sealed or laminated to form discrete compartments.

According to another aspect of the disclosure, the foam layer may be impregnated with a water based herbal solution. This solution may include witch hazel, aloe vera, lavender, calendula extract, chamomile and/or any other suitable herbal ingredient(s). In some embodiments, the pad remains flexible and conformable, even when frozen. In other embodiments, when the pad is frozen, it maintains a specific pre-molded shape that it was frozen in, and the pre-molded shape may be configured to keep physical pressure off areas of the perineum that are most injured. Molds, forms, and/or manual shaping of the pad by the user may be used to achieve a desired shape. In some embodiments, the pad remains flexible and conformable, even when frozen. In various embodiments, the water based herbal solution may have a viscosity of about 400-1400 cps (centipoise), which provides a gel like consistency but allows passive diffusion of the solution through the foam pad to give a uniform saturation. In other embodiments, the pad may be saturated with the herbal based solution to between about 60% and about 100% of the total saturation capacity of the pad.

In some embodiments, the pad may be combined in various fashions, such as indwelling, dry or wet coating, soaked, wicked, and/or any combination thereof, to include one or more combinations of pharmacological ingredients, herbal ingredients, inactive ingredients, and/or pad materials. Such combinations may facilitate delivery of ingredients to the perineal area and surrounding anatomical structures.

In another aspect of this disclosure, a pad for treating a perineal area of a woman before or after childbirth may include an open cell foam layer having a thickness in a range of 1 millimeter to 300 millimeters and a width to fit within the perineal area and a substance integrated with the foam layer. The foam layer is flexible, such that it can conform to the perineal area of the woman. The substance may be integrated with the foam layer by a method such as but not limited to saturating, coating, soaking, or spraying.

In some embodiments, the substance may be an herbal ingredient, such as but not limited to lavender, chamomile, calendula, tea tree oil, cucumber extract, menthol, ethanol, alcohol, eugenol, peppermint oil, sunflower seed oil, aloe vera, hemp and/or hemp oil, green tea and other kinds of tea, coconut and coconut oils, turmeric, sage, feverfew, coneflower, mint, cilantro, lemon balm, Mullein, cinnamon, witch hazel, lanolin, marshmallow root, beeswax, or almond seed oil. In various embodiments, the substance may be a solution, a gel, an aerosol, a liquid, or a coating. In various embodiments, the substance is configured to serve a therapeutic purpose, such as but not limited to pain reduction, anti-inflammatory, postpartum depression reduction, anti-constipation effects, anti-infective effects with aseptic properties, anti-itch, reduction of infection risk, swelling reduction or bleeding reduction. Some embodiments may include multiple different substances.

In various embodiments, the foam layer may be made of a material such as but not limited to polyurethane, felt, neoprene, polyester, foam rubber, polystyrene, XPS foam, polyvinyl chloride, EVA-PE foams, silicone foams, cellulose and/or paper based foams or celled structures for wicking/liquid retention, polyethylene, shape memory foam polymers, paper, pulp, cotton, polycotton, viscose, asahi nylon, bamboo, polyacrylamide, poly(N-isopropylacrylamide), polyethylene glycol, collagen, agarose, hyaluronic acid, poly(organophosphazenes), chitosan, polyacrylic acid, polymethylmethacrylate, poly(2-(dimethylamino) ethyl methacrylate), poly(2-(diethylamino) ethyl methacrylate), or poly(2-vinylpyridine).

In some embodiments, the pad further includes a skin contact layer attached to one side of the foam layer and including a non-absorbent material, to provide a barrier between skin of the perineal area and the foam layer. In some embodiments, the skin contact layer includes multiple perforations to allow flow of fluid through the skin contact layer.

In some embodiments, the foam layer includes at least one opening extending through the thickness of the foam layer. In some embodiments, for example, the foam layer includes multiple openings, such as but not limited to slits and/or perforations. Generally, the foam layer is flexible enough when frozen to be molded to fit the perineal area. In some embodiments, the thickness of the foam layer is in a range of 1 millimeter to 30 millimeters.

In another aspect of the present disclosure, a method for treating a perineal area of a woman before or after childbirth involves applying a pad to the perineal area, where the pad includes an open cell foam layer having a thickness of between 1 millimeter and 300 millimeters and a width to fit within the perineal area, and a substance integrated with the foam layer. The woman then leaves the pad in place on the perineal area for a period of time. The method may further involve freezing the pad before applying the pad to the perineal area. Alternatively, the method may involve cooling the pad without freezing it, before applying the pad to the perineal area. In another alternative embodiment, the method may involve heating the pad before applying it to the perineal area. The method may also involve molding the pad to fit a shape of the perineal area. In some embodiments, the method may involve applying the substance to the foam layer before applying the pad to the perineal area. The method may also involve removing the pad from a sealed package in which the substance has combined with the foam layer.

In another aspect of the present disclosure, a pad for treating a perineal area of a woman before or after childbirth may include: a skin contact layer; a foam layer coupled with one side of the skin contact layer; and a substance integrated with the foam layer. The skin contact layer and the foam layer are flexible, to allow them to conform to the perineal area of the woman.

In another aspect of the present disclosure, a method for making a perineal pad for treating a perineal area of a woman before or after childbirth may involve providing an open cell foam layer having a thickness in a range of 1 millimeter to 300 millimeters and a width to fit within the perineal area, applying a substance to the foam layer and allowing the substance to permeate partway into the foam layer, and sealing the foam layer inside a sealed package to allow the substance to further permeate into the foam layer within the sealed package over time. In various embodiments, the substance is applied to the foam layer by a method such as but not limited to saturating, coating, soaking, or spraying. In some embodiments, multiple substances may be applied to the foam layer.

These and other aspects and embodiments are described in greater detail below, in relation to the attached drawing figures.

DETAILED DESCRIPTION

The various embodiments of the device and method involving the pads described in this disclosure may be altered in any number of different ways, without departing from the scope of the invention as described in the claims. Specific examples of devices and methods are provided primarily for illustrative purposes and should not be interpreted as limiting the scope of the invention. For example, although the devices and methods are primarily described herein for use in relieving pain and discomfort in the perineal area after childbirth, the same or similar devices and methods may be used in the perineal area before childbirth or on other parts of the body to relieve pain and discomfort from causes other than childbirth.

In some embodiments, a pad for application to the skin in the perineal area may combine cold therapy with therapy provided by a substance integrated with the pad (e.g., an herbal substance) for treating pain and/or discomfort. Cold therapy and herbal therapy, for example, are both useful tools in managing perineal discomfort, swelling and pain in the days and weeks after a woman gives birth. Currently, however, no single device provides the benefits of cold and herbal therapy together in a way that is comfortable and conformable, while protecting the skin from damage from direct contact with frozen material. Some embodiments described herein may also deliver some amount of a therapeutic substance to the skin in the perineal area, for example a wet, fluid, semifluid, foam, liquid, active pharmaceutical ingredient, herbal ingredient, gel, or other type of therapeutic substance.

One embodiment of the pad described herein includes a layer of foam material ("the foam layer") that is saturated, coated, soaked, sprayed, or otherwise manufactured to contain some portion of a solution, gel, aerosol, liquid, coating, or other substance(s) or herbal extract(s), at concentrations characterized as safe for use on the sensitive perineal area and suitable for application to the skin to provide therapeutic benefits. In alternative embodiments, the material may be something other than a foam material, such as but not limited to a sheet, gel, or other absorbent, non-absorbent, semi-absorbent or eluting material. In this disclosure, the terms "pad," "perineal pad," and "freezable pad" may be used interchangeably to refer to the devices being described. In some embodiments, the pad might not be freezable—for example, some embodiments may be designed for delivering heat therapy rather than cold therapy.

For ease of understanding and description, the phrase "integrated with" (or "integrated into") will be used generally to describe any of the ways in which a substance might be combined with or impregnated into one or more portions of the perineal pad—e.g., saturated, coated, soaked, sprayed, etc. Therefore, "integrated with" or "integrated into" encompasses all of the different possible methods for combining one or more substances with a perineal pad, and the long list of possible ways to integrate the substance into the device will not be repeated with the description of each embodiment.

The term "substance" (or "therapeutic substance") is generally used in this application to refer to any of the herbal, pharmacological or other substances, as well as combinations of substances, described in this application. According to various embodiments, the substance may take the form of an aerosol, liquid, gel, or solid.

The substance integrated with the perineal pad may serve any suitable therapeutic purpose, including but not limited to pain reduction, anti-inflammatory, postpartum depression reduction, anti-constipation effects, anti-infective effects with aseptic properties, anti-itch, reduction of infection risk, swelling reduction and/or bleeding reduction. One or more herbal ingredients may be included in an aqueous or non-aqueous solution, gel, aerosol, sprayed substance, coated substance, or other delivery or holding medium, to combine the ingredient(s) with the pad for delivery. Examples of herbal, natural or semi-natural ingredients that may be used in a perineal pad include, but are not limited to lavender, chamomile, calendula, tea tree oil, cucumber extract, menthol, ethanol, alcohol, eugenol, peppermint oil, sunflower seed oil, aloe vera, hemp and/or hemp oil, green tea and other kinds of tea, coconut and coconut oils, turmeric, sage, feverfew, coneflower, mint, cilantro, lemon balm, Mullein, cinnamon, witch hazel, lanolin, marshmallow root, beeswax, almond seed oil and any combination thereof. Other substances in the pad may include, but are not limited to, anti-inflammatory or pain relieving drugs (ibuprofen or NSAIDs, lidocaine, benzocaine, acetocaine, tetracaine, prilocaine, menthol, morphine, oxycodone, acetaminophen, ethanol, cannabinoids/cannabis, CBD oils, hemp oils, paracetamol, codeine, Nefopam, Flupirtine, Ziconotide), anticonvulsant drugs (carbamazepine, gabapentin, pregabalin, gabapentinoids, and others including those used to treat neuropathic pain), vasoconstrictors (pseudoephedrine, epinephrine, Phenylephrine), anti-depressants (tricyclic antidepressants, lithium), vitamins and their derivatives (vitamin D2 and D3, vitamin C, ascorbyl palmitate, ascorbic acid, vitamin E, argan oil), birth preparatory/ripening agents (dinoprostone/prostaglandins/CERVIDIL), antibiotics, progesterone, other anti-inflammatory agents (capsaicin, resveratrol), stool softeners/laxatives, menthol, silver, oxytocin/Pitocin, and/or any other substance that has a therapeutic effect which may be achieved through local delivery to the surface around the perineal area, reproductive area, and/or urinary or rectal openings.

Some therapeutic uses of the pad include, but are not limited to, reducing swelling and/or pain, treating hemorrhoids, reducing urinary tract infection (UTI) risk, reducing group B strep risk, cancer treatment, period pain, labor induction, abdominal cramps, gastrointestinal disease treatment, C-section recovery or preparation, pre-birth preparation, and other medical indications. As mentioned above, these uses are not limited to postpartum perineal injuries, and in some cases the perineal pad may be used only before childbirth or before and after childbirth. The therapeutically active ingredients may be included or formulated alone to be delivered by the device, with or without a carrier material, such as a solution of buffered aqueous medium and/or other excipients. Alternatively or additionally, the therapeutically active substance may be included to work synergistically or separately with a co-formulation of other herbal or natural ingredients, which are not entirely inert excipients as described herein. In addition, the natural or herbal ingredients may be used alone in the pad device, or alternatively they may be combined with a carrier material and/or therapeutically active ingredient(s) in solution.

In some embodiments, the pad may be constructed so that a first part of the pad includes a first substance, and a second part of the device a second substance, such that these two substances do not substantially mix during storage and may be delivered together or independently after the device is removed from packaging and placed against the target area for therapy. In such embodiments, a surface coated tape or removable cover may be used to prohibit the escape of the substances from their section of pad prior to use. Alternatively, in another embodiment, the pad may be configured with walls, cells or sealed sections, at least in some part(s) of the pad, such that multiple substances may be isolated from one another. This again allows for multi-substance delivery during use.

In other such embodiments, the pads may be loaded with multiple substances, which when exposed to each other through the action of breaking a seal or opening the package or exposing the pad to the external environment of oxygen, heat from the body, pH difference in the perineal area, light or other catalyst, the reaction of the substances with the stimulus and/or each other causes a desired therapeutic effect. For example, in one embodiment, the pad may include citric acid in one compartment and baking soda in another compartment. At some point just before or after applying the pad to the skin, the citric acid is allowed to combine with the baking soda to cause an endothermic reaction, which reduces the temperature of the pad for a period of time, providing cooling therapeutic benefit without needing to pre-freeze the pad. Other possible reactive substances include, but are not limited to, sodium acetate, barium hydroxide and ammonium thiocyanate. Depressurizing a gas cylinder against the pad through a vented connection is another exemplary method to induce a cooling/freezing effect within the pad, without needing to place the pad in the freezer. In other embodiments, exothermic reactions may be caused by mixing two (or more) substances in the pad or by exposing a single or multiple substances in the pad to light, heat, oxygen, or a pH change from the wound environment. Examples of substance used to generate such exothermic reactions include, but are not limited to activated carbon, water and iron; and solutions of supersaturated crystalline fluids, such as sodium acetate and a nucleation site to enable the dissolved substance to crash out of solution and create an exothermic release.

The pad (or other support medium) may include any one or more of the substances mentioned above. Alternatively or additionally, the pad may include water or one or more other inert substances, such as a gelling agent (e.g., polyethylene glycol, gelatin, polyacrylate) or a hydrogel generating substance. In embodiments in which a substance is (or multiple substances are) integrated with the pad, the pad itself may be constructed of one or more types of a foam or foam-like material. The pad may include one layer or multiple layers, horizontal or vertical sections, or other more complex secondary shapes, with reservoirs and various materials with sections of sealed and unsealed foam compartments, for example a combination of open and/or closed cells. Typically, the pad includes a mechanism for integrating one or more therapeutic substances within it. Examples of foam and foam-like materials that may be used in the pad include, but are not limited to, polyurethane, felt, neoprene, polyester, foam rubber, polystyrene, XPS foam, polyvinyl chloride, EVA-PE foams, silicone foams, cellulose and/or paper based foams or celled structures for wicking/liquid retention, polyethylene, shape memory foam polymers, and/or composites thereof. In other embodiments, the pad may include one or more alternative materials with wicking and/or absorbent properties, such as paper, pulp, cotton, polycotton, viscose, asahi nylon, bamboo, or the like. In other embodiments, the pad material may include a hydrogel, such as but not limited to polyacrylamide, poly(N-isopropylacrylamide), polyethylene glycol, collagen, agarose, hyaluronic acid, poly(organophosphazenes), chitosan, polyacrylic acid, polymethylmethacrylate, poly(2-(dimethylamino) ethyl methacrylate), poly (2-(diethylamino) ethyl methacrylate), or poly(2-vinylpyridine). These may be configured to release a substance under predetermined conditions of pH, temperature, electrostatic charge, pressure, and/or the like.

Figure 1:
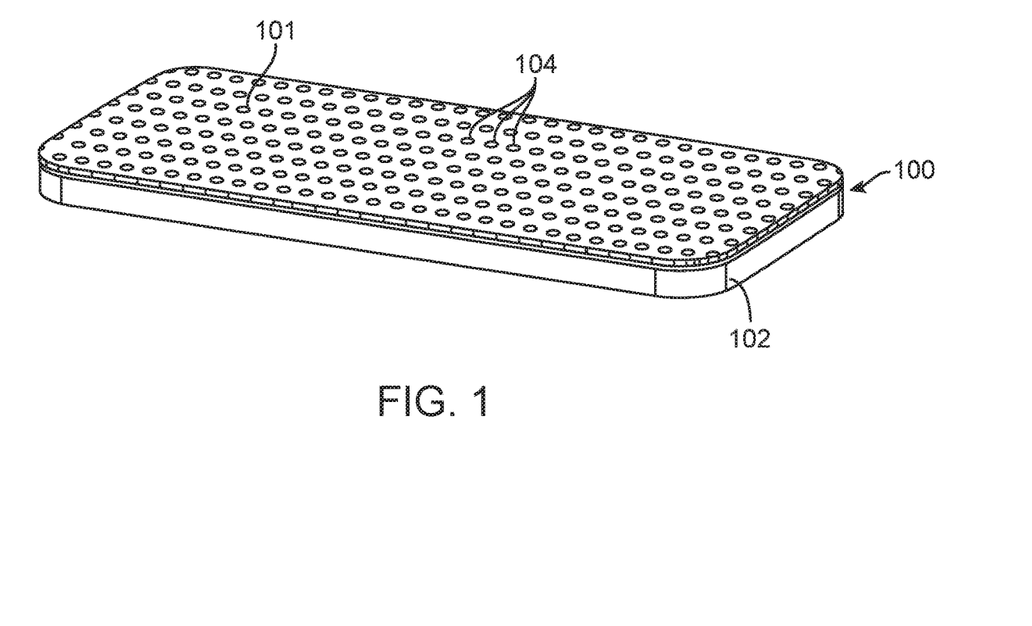
FIG. 1 is a perspective view of a freezable impregnated pad, according to one embodiment.
Figure 2:
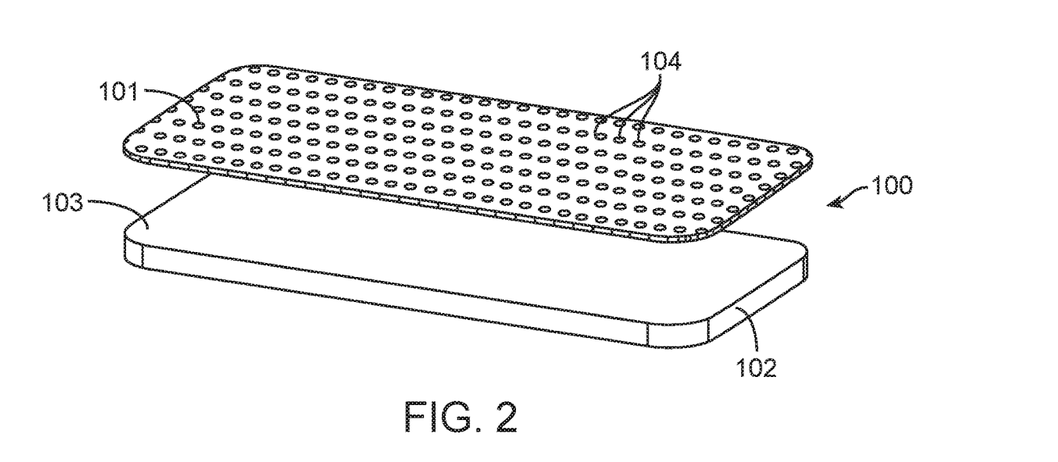
FIG. 2 is an exploded perspective view of the freezable impregnated pad of FIG. 1.
Figure 3:
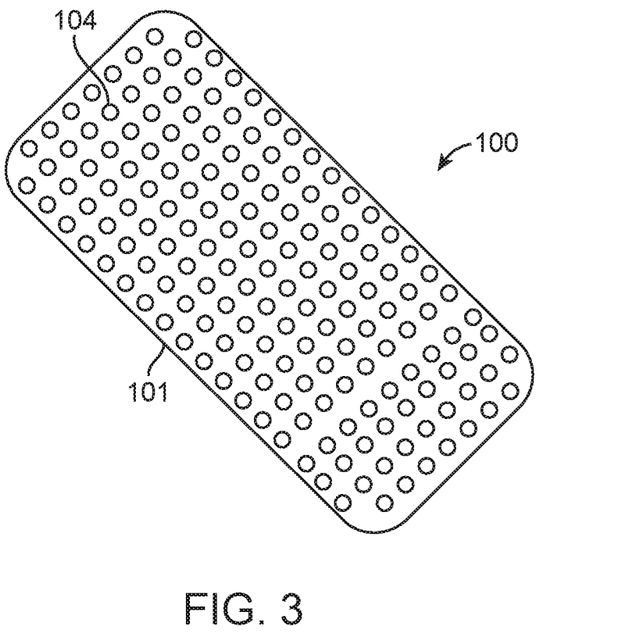
FIG. 3 is a top view of a skin contact layer the freezable impregnated pad of FIGS. 1 and 2.

FIGS. 1-3 are perspective, exploded and top views, respectively, of one example of a therapeutic perineal pad 100. In this embodiment, the pad 100 includes an upper, skin contact layer 101, with multiple perforations 104 in it, and a lower, foam layer 102, which is integrated with a substance 103 (e.g., solution, gel, foam, coating, and/or any of the substance described above). As mentioned above, the phrase "integrated with" encompasses any suitable mechanism for coupling the substance 103 with the foam layer 102. For example, the foam layer 102 may be absorbent and hold the substance 103 in that way, or the foam layer 102 may be configured as a reservoir (or multiple reservoirs) to hold the substance 103 and (optionally) release it, or the foam layer 102 may be coated with the substance 103. These are merely three examples, and any other suitable way for integrating the substance 103 with the foam layer 102 may be used in any given embodiment. Any suitable substance 103 or combination of substances 103 may be used in the pad 100, including but not limited to those listed above and below. The skin contact layer 101 and the foam layer 102 may be bonded together. The pad 100 may be contoured to comfortably fit the perineal area while maintaining skin contact.

In this embodiment, the skin contact layer 101 may be constructed from a non-absorbent or low-absorbent material, so the skin contact layer 101 provides a barrier between the substance 103, which may for example be a water-based herbal solution, and the patient's skin. The skin contact layer 101 also helps protect the skin from damage though direct contact with frozen material. In some embodiments, the skin contact layer 101 may be a film or a different layer of foam than the foam layer 102.

Referring to FIG. 3, in some embodiments, the skin contact layer 101 includes multiple perforations 104 (or "openings"), to allow liquids to pass in both directions through the skin layer 101. Each of the perforations 104 may have any suitable shape and size. In the illustrated embodiment, for example, the perforations 104 are circular, and in various embodiments, each perforation may have a diameter of about 0.01 mm to about 10.00 mm. As illustrated in FIG. 3, in some embodiments, the perforations 104 may be uniformly spaced along the entire surface of the skin contact layer 101 in a grid pattern. In some embodiments, the foam layer 102 may have the same or similar perforations as those of the skin contact layer 101.

Figure 4:
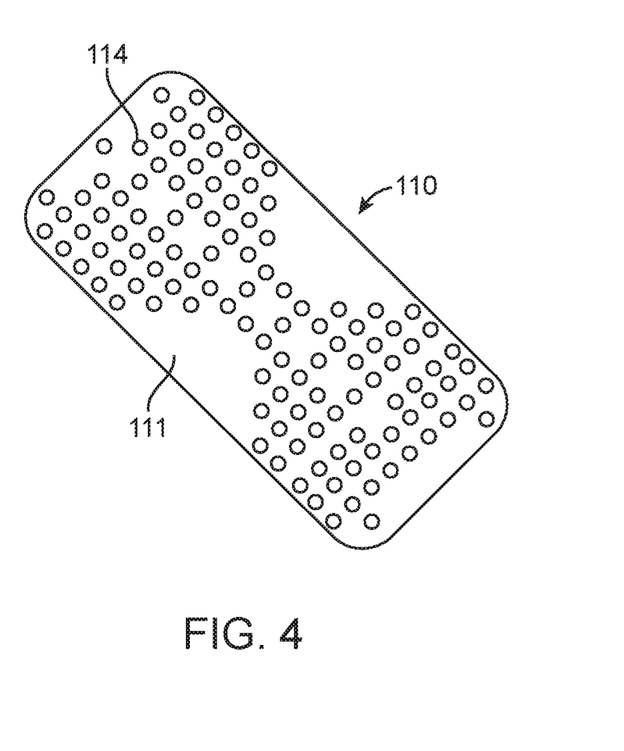
FIG. 4 is a top view of a skin contact layer of a freezable impregnated pad, according to an alternative embodiment.

Referring to FIG. 4, in an alternative embodiment, the skin contact layer 111 of a therapeutic perineal pad 110 may include perforations 114 laid out in a different pattern. The pattern, such as the hourglass shape in the illustrated embodiment, may be configured to divert liquid through the skin contact layer 111 without compromising contact between the pad 110 and skin in the perineal area.

Figure 5:
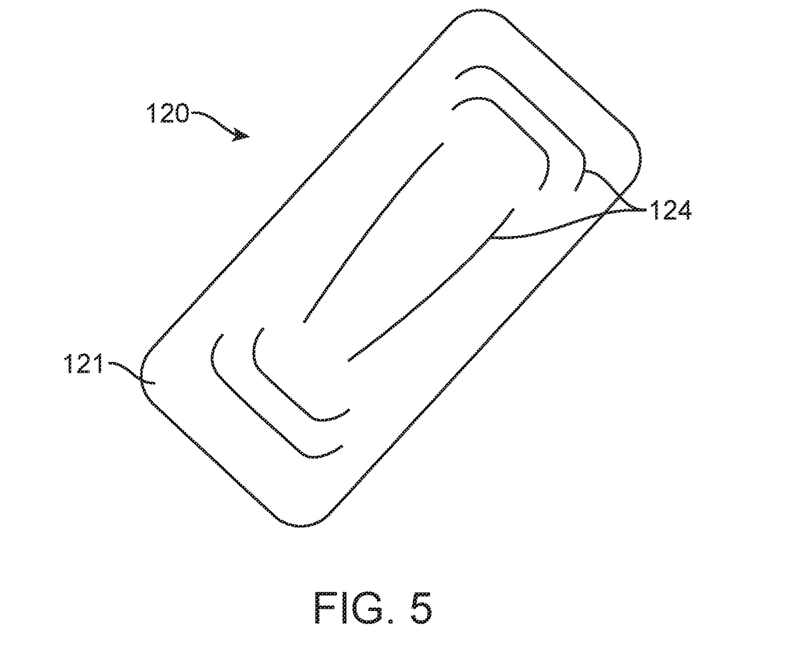
FIG. 5 is a top view of a skin contact layer of a freezable impregnated pad, according to another alternative embodiment.

FIG. 5 is a top view of another embodiment of a therapeutic perineal pad 120, in which the skin contact layer 121 includes multiple slits 124, rather than the round perforations of the previous embodiments. Other embodiments may include any number, size, shape, pattern or configuration of perforations, slits, apertures and/or other openings. In some embodiments, the openings may pass all the way through the skin contact layer 121, while in alternative embodiments they may pass only partway through the skin contact layer 121. Again, the foam layer (not shown) may have the same or similar slits as those of the skin contact layer 121. In one alternative embodiment, the perineal pad 120 may include only a foam layer and no skin contact layer 121, and the foam layer may include the slits 124 illustrated in FIG. 5.

Figure 6:
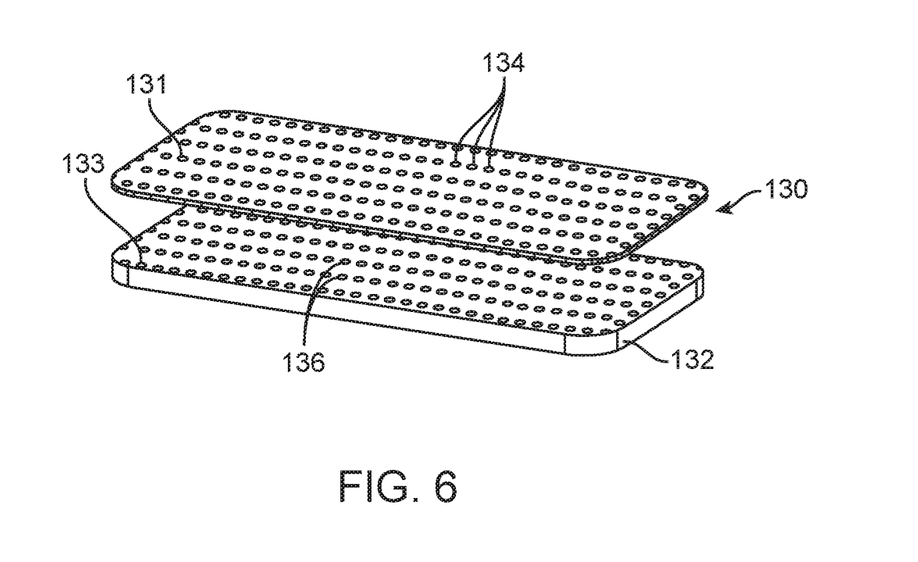
FIG. 6 is an exploded perspective view of a freezable impregnated pad, according to another alternative embodiment.

Referring to FIG. 6, an exploded view of another alternative embodiment of a therapeutic perineal pad 130 is provided. This embodiment also includes a skin contact layer 131, a foam layer 132 and an integrated substance 133. In this embodiment, the skin contact layer 131 includes perforations 134, and the foam layer 132 also includes perforations 136. In various embodiments, the foam layer 132 may be a reticulated, open cell foam (or "open pore foam"), optimized to allow heat/cold and/or moisture exchange. One such embodiment may include a foam layer 132 with a thickness of about 1 mm to about 300 mm (dry, unsaturated), or in some embodiments about 1 mm to about 30 mm, such that it would remain flexible and conformable when hydrated and frozen.

In one embodiment, the substance 133 in the foam layer 132 may be a water based solution containing witch hazel, aloe vera and water. The solution may have a concentration of witch hazel of about 0.1 percent to about 80 percent weight per volume and a concentration of aloe vera of about 0.1 percent to about 80 percent weight per volume. In an alternative embodiment, the substance 133 may be alcohol based instead of water based. In alternate embodiments of both the water-based and alcohol-based embodiments, other herbal additives with known therapeutic benefit may be included at low concentrations (e.g., less than 10 percent). Examples of such additives include, but are not limited to, lavender, chamomile, calendula, tea tree oil, cucumber extract, menthol, eugenol, peppermint oil, and almond seed oil. In alternate embodiments, the substance 133 may be (or include) an active medicinal agent, to deliver a topical analgesic effect. Examples of such medicinal agents include, but are not limited to, Lidocaine, Benzocaine, Lignocaine, Cocaine Dibucaine, Dyclonine, Prilocaine, Articaine, Bupivacaine, Xylocaine, Etidocaine, Mepivacaine, Chloroprocaine, Procaine, and Tetracaine.

In another alternative embodiment, the substance 133 may combined with or substituted by a solution containing one or more active antimicrobial agents, to prevent infection and/or manage microbial bioburden in the perineal area. Examples of such antimicrobial agents include, but are not limited to, iodine, Chlorhexadine, honey, PHMB, silver compounds (e.g., silver nitrate or silver acetate), hyaluronic acid, and octenidine. Additional inclusions or adjustments or substitutions to create further therapeutic benefits with the substance 133 may be provided by adding alternative materials, such as those described herein for alternative therapeutic benefits.

Figure 7:
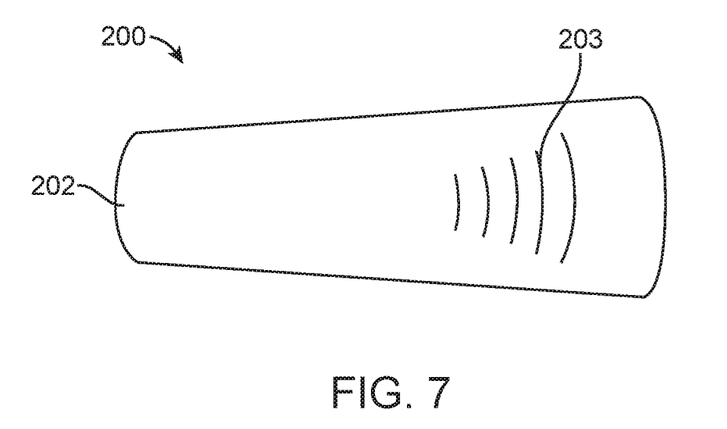
FIG. 7 is a top view of a freezable impregnated pad, according to another alternative embodiment.

FIG. 7 is a top view of another example of a freezable, impregnated pad 200. In this embodiment, the pad 200 includes an open cell foam layer 202, which is saturated with a substance (solution, etc.). The pad 200 also includes slits 203 and is contoured to fit the perineal area comfortably while maintaining skin contact. For example, in this embodiment, the pad 200 is tapered from a wider end to a narrower end, with the slits 203 being positioned closer to the wider end. Additionally or alternatively, the pad 200 may include any other type of openings or apertures that extend through the thickness of the foam layer 202, such as but not limited to perforations. The foam layer 202 has a width and shape to fit comfortably within the perineal area and a thickness configured to help contain the substance(s) integrated into it and to maintain a cold temperature for a period of time to provide relief of discomfort and/or pain. In various embodiments the thickness of the foam layer 202 may range from about 1 millimeter to about 300 millimeters, or more preferably from about 1 millimeter to about 30 millimeters.

Figure 8:
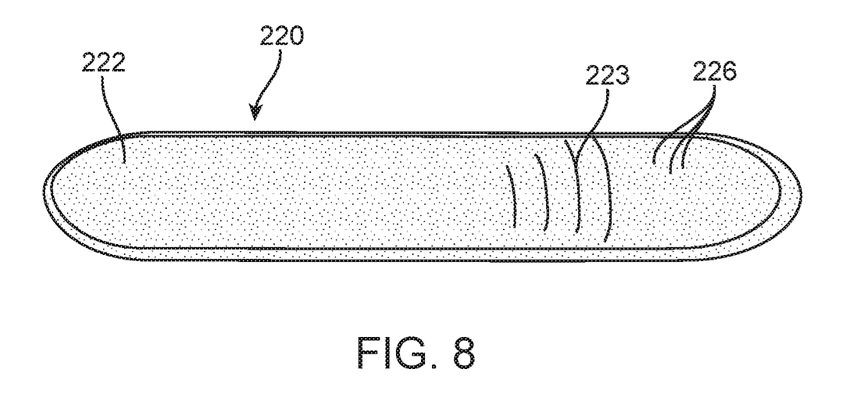
FIG. 8 is a perspective view of the freezable impregnated pad of FIG. 7.

Referring to FIG. 8, another embodiment of a freezable, impregnated pad 220 is illustrated. In this embodiment, the pad 220 includes a foam layer 222 with slits 223 and perforations 226 arrayed in a uniform grid pattern. The slits 223 and perforations 226 allow transfer of liquids in both directions. The slits 223, for example, may have a diameter of about 0.01 mm to about 10.00 mm, and a length of about 0.05 mm to about 100.00 mm. As illustrated in FIG. 8, the slits 223 may be spaced to divert any flow of liquid (such as blood from the perineal area) through the foam layer 222, without compromising contact between the pad 220 and skin in the perineal area. In an alternative embodiment, the slits 223 may be uniformly distributed across the whole pad surface. Other embodiments may include any number, size, shape, pattern or configuration of perforations 226, slits 223 and/or the like. The perforations 226 may extend completely through the foam layer 222, from one side to another, or alternatively may only extend partially through the foam layer 222. In some embodiments, some perforations 226 may extend all the way through the thickness of the pad 220, while others extend only partway. This "indenting" of the pad allows for part of the pad in one direction to include some surface material, closed or open cell foam, or other partially or fully obstructive material.

In various embodiments, the foam layer 222 may be a reticulated, open pore foam, optimized to allow heat and moisture exchange. For example, the foam layer 222 may be made of PU, PVA, Polyether, Polyester or other polymer foam with similar properties. As mentioned above, the foam layer 222 may have a thickness of about 1 millimeter to about 30 millimeters or as much as about 300 millimeters (dry, unsaturated), and it may remain flexible and conformable even when hydrated and frozen. The foam may include hydrophilic properties to allow passive, uniform diffusion of any aqueous fluid applied to its surface. In some embodiments, the surface of the foam layer 222 may be perforated to a depth of about 0.2 mm to about 2.5 mm, for example by using a needle roller to channel the substance (e.g., herbal solution), increase absorbency and ensure uniform diffusion of the substance. Alternatively, a die cutter may be used during manufacture to create wells/depressions of a depth of about 0.2 mm to about 2.5 mm in the surface of the foam layer 222 to give a similar result. The foam layer 222 may be integrated with (contain, hold, be saturated with, be coated with, etc.) any of the substances described above or below.

In various embodiments, the viscosity of the substance integrated with the foam layer 220 may be about 400 cps to about 1400 cps, a gel like consistency which is still able to passively saturate the foam though diffusion. Examples of thickening agents that may be used to provide the substance with this viscosity include, but are not limited to, cellulose gum, aloe vera gel, xantham gum, rice starch, carbomer, guar gum and gelatin.

Figure 9:
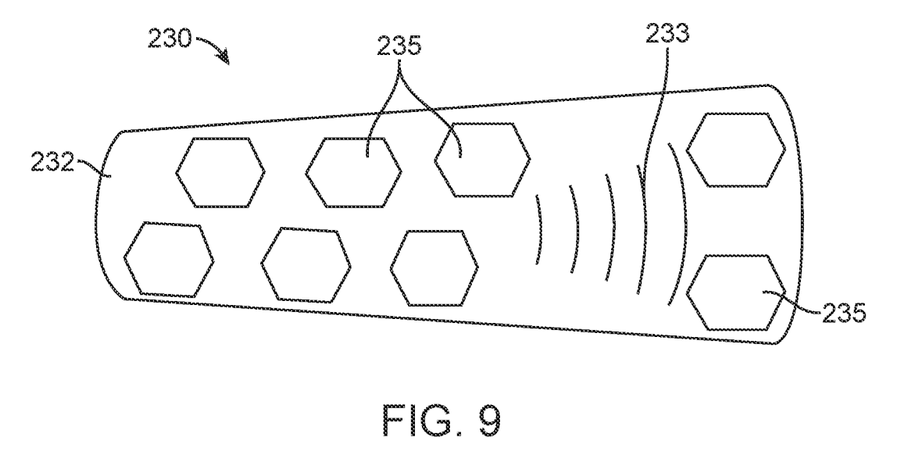
FIG. 9 is a top view of a freezable pad with discrete sealed compartments, according to one embodiment.

Referring to FIG. 9, another embodiment of a therapeutic perineal pad 230 is illustrated in top view. In this embodiment, the edges of the foam layer 232 may be sealed, for example using heat or chemical lamination, resulting in a physical barrier to the flow of liquid. This embodiment of the foam layer 232 also includes discrete sealed subsections 235 within the open cell foam, which may be either fully or partially sealed to form the sealed subsections 235. These discrete subsections 235 may be free from herbal solution and in some embodiments may be specifically dosed with the active medicinal agents, active antimicrobial agents, other types of active ingredients, or a combination of thereof. In various embodiments, the closed subsections 235 may be of any number, shape, size and pattern of distribution.

Figure 10:
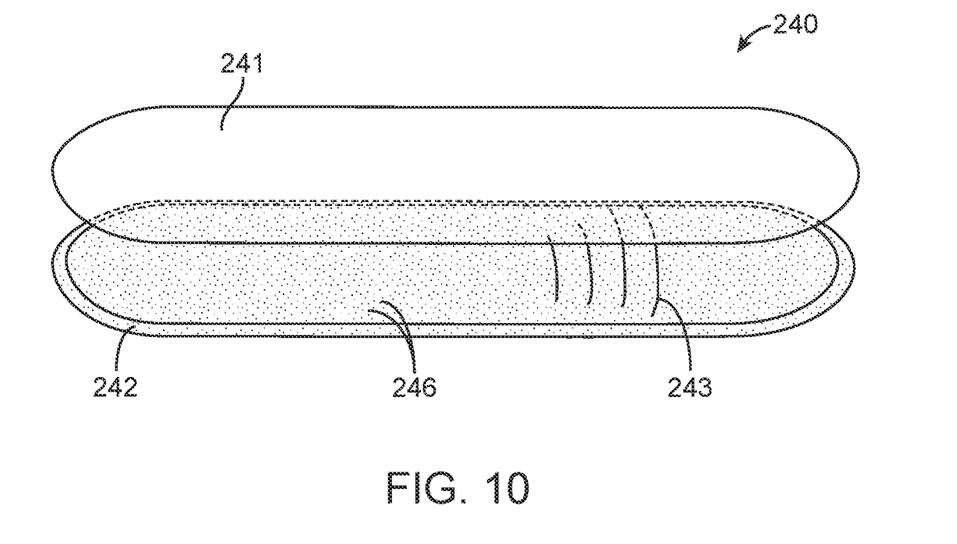
FIG. 10 is an exploded perspective view of a freezable pad with multiple layers, according to an alternative embodiment.

Referring to FIG. 10, in another embodiment, a perineal pad 240 may include a top layer 241 (or "first layer"), which is laminated or bonded to a bottom layer 242 (or "second layer"). The bottom layer 242 may include perforations 246 and/or slits 243. The bottom layer 242 may be constructed from a non-absorbent or low-absorbent material, to provide a barrier between the substance (e.g., water based herbal solution) and the skin. In one example, the bottom layer 242 may be Polyurethane (PU), either as a film or a foam layer. In other embodiments, the bottom layer 242 may be made of any of a number of other suitable polymers, such as but not limited to Polyethylene, PVA, Polyester, sheet hydrogel, or a natural woven or non-woven material, such as cotton, polycotton, viscose, rayon, asahi nylon, or bamboo.

Figure 11:
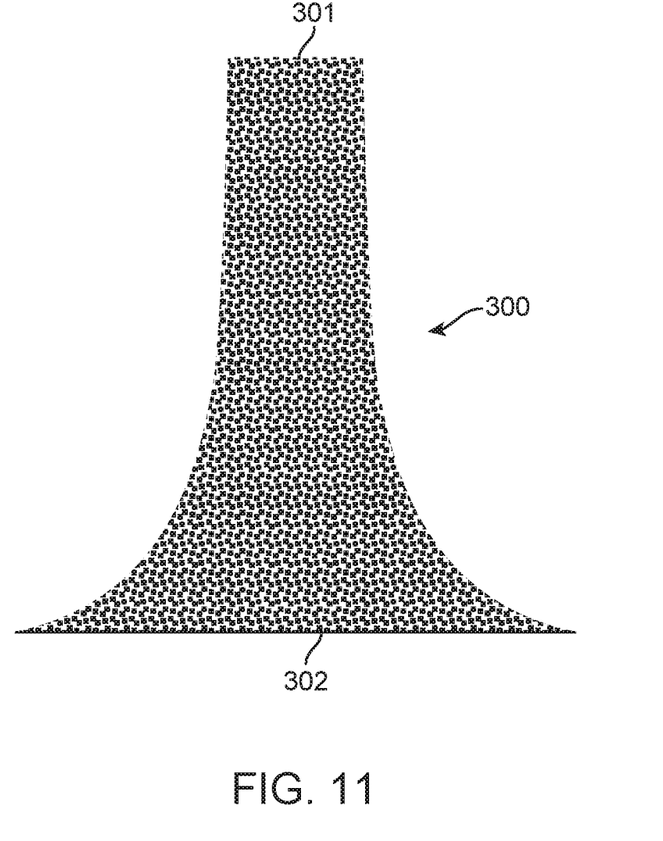
FIG. 11 is a top view of a tapered, freezable pad, according to another alternative embodiment.

Referring to FIG. 11, in another embodiment, a therapeutic perineal pad 300 (or foam layer thereof) may be shaped specifically to provide targeted relief to the anorectal area, rather than the perineal area as a whole. Thus, the pad 300 may have a shape that widens from a narrow end 301 to a wide end 302. In some embodiments, for example, the narrow end 301 may have a width of about 1 mm to about 20 mm, and the wide end 302 may have a width of about 20 mm to about 100 mm. This shape of the pad 300 is ergonomically designed to hold the pad in place in the intergluteal cleft against the anus.

Figure 12:
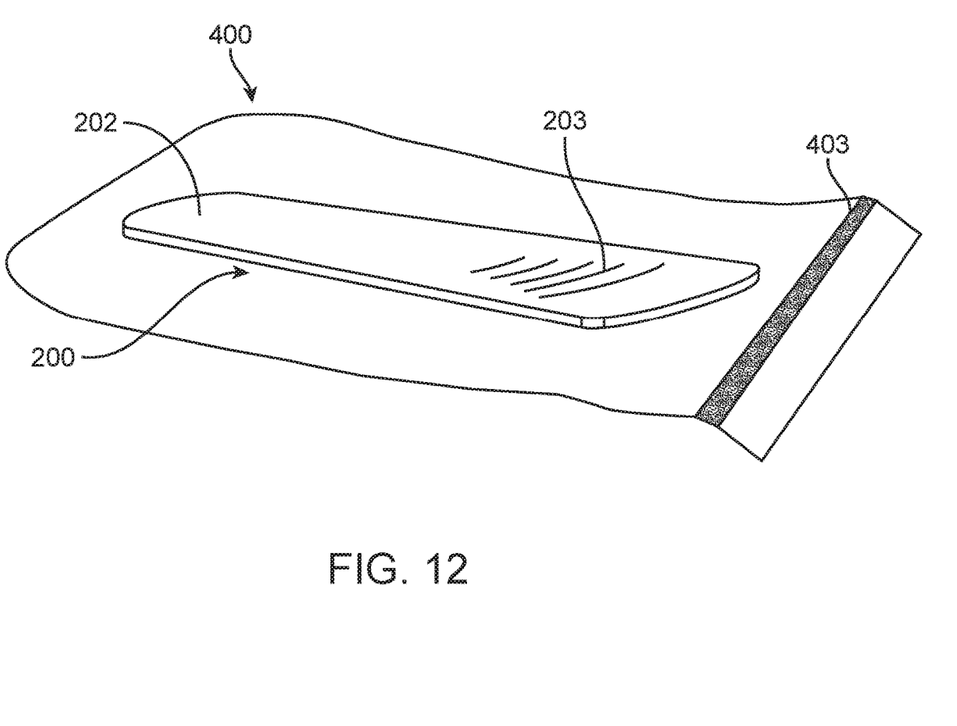
FIG. 12 is a perspective view of a freezable pad in a sealed package, according to another alternative embodiment.

FIG. 12 is a perspective view of the therapeutic perineal pad 200, packaged in a sealable pouch 400. Any of the pad embodiments described herein may be packaged in such a sealable pouch 400. The pad 100 and any alternative embodiments thereof may be provided in any suitable packaging, which may enhance shelf life, transport and/or ease of use of the pad 200 by the user. In various embodiments, the pouch 400 may be made of any suitable plastic and may include a re-sealable seal 403, such as a Ziploc® seal. The pad 200 is saturated with (or otherwise coupled with) a substance (e.g., solution, gel, foam, coating, etc.) inside the pouch 400. The foam layer 202 of the pad 200, residing in the pouch 400, allows a fluid, powder, or other material to passively diffuse into the foam while the pad 200 is in transit. In addition, active diffusion may occur through the action of applying pressure or oscillations in atmospheric pressure to the pouch 400 (and thus the substance to be diffused and the foam layer 202), in order to facilitate uniform distribution of the substance throughout the desired regions of the foam layer 202. In fact, one method of manufacturing and packaging the pad 200 involves providing the pad 200, applying a substance (or substances) to the foam layer 202 to let the substance partially permeate the foam layer 202, placing the foam layer 202 in the pouch 400, sealing the pouch 400, and then allowing the substance to further permeate the foam layer 202 during transit and/or storage. The method may be enhanced by applying pressure and/or otherwise manipulating the pouch 400 and the pad 200 to further integrate the substance with the foam layer 202.

In some embodiments, not all regions of the foam layer 202 are exposed to the substance. For example, heat sealing of open cells of the foam layer 202 or coatings may provide for targeted diffusion of the substance to a specific area within the foam layer 202 while it is in the pouch 400, prior to being inserted into the pouch 400, or after being exposed to a natural environment when removed from the package 400. The pouch 400 may also include the seal 403, to protect the pad 400 from exposure to air and/or pathogens, while protecting contents inside, such as moisture, the foam layer 202, and/or any diffusing agents soaked into the foam layer 202. In alternative embodiments, the pouch 400 may simply be torn open and not re-sealable. The seal 403, or alternative seals, may be made by heat sealing or heat molding compression or other method, such as ultrasonic welding.

For any freezable or cooled embodiments of the perineal pad described herein, the pad may be cooled from an exogenous source in situ, rather than being pre-frozen. This may be achieved, for example, through combination of a room temperature or chilled pad (e.g., about 2-7 degrees Celsius or below), with a secondary frozen cold therapy gel pad to give the therapeutic effect.

In use, the woman may place the pouch 400 with the pad 200 inside into the freezer to freeze, or for alternative embodiments into a refrigerator or other cooling mechanism. After the pad 200 is frozen, the woman removes the pouch 400 from the freezer, opens the pouch 400, and applies the pad 200 to her perineal area. She will then leave the pad 200 in place for a period of time, to help relieve the discomfort and/or pain in the area. The pad 200 may be placed in direct contact with the woman's skin, underneath an undergarment such as postpartum underpants or the like. When the pad 200 is no longer providing relief or the woman no longer wants to wear it, she can simply throw it away. Alternatively, in some embodiments, the pad 200 may be reusable and may be refrozen for a number of times.

Although the foregoing description is believed to be accurate, it is provided for exemplary purposes and is not intended to limit the scope of the invention as described by the following claims. Features of any embodiment described above may be applied to other embodiments, for example, without departing from the scope.

We claim:

1. A pad for treating a perineal area of a woman before or after childbirth, the pad comprising:
   an open cell foam layer having a width to fit within the perineal area; and
   a substance having a viscosity of at least 400 centipoise integrated with the open cell foam layer which provides a gel like consistency and allows passive diffusion of the substance through the open cell foam layer to give a uniform saturation, the substance comprising witch hazel, aloe vera, and water;
   wherein the open cell foam layer has a thickness of about 1 millimeter to about 30 millimeters such that the open cell foam layer is flexible and can conform to the perineal area of the woman when hydrated and frozen.

2. The pad of claim 1, wherein the substance is integrated with the open cell foam layer by a method selected from the group consisting of saturating, coating, soaking, and spraying.

3. The pad of claim 1, wherein the substance is configured to serve a therapeutic purpose selected from the group consisting of pain reduction, anti-inflammatory, postpartum depression reduction, anti-constipation effects, anti-infective effects with aseptic properties, anti-itch, reduction of infection risk, swelling reduction and bleeding reduction.

4. The pad of claim 1, wherein the open cell foam layer comprises a material selected from the group consisting of polyurethane, felt, neoprene, polyester, foam rubber, polystyrene, XPS foam, polyvinyl chloride, EVA-PE foams, silicone foams, cellulose or paper based foams or celled structures for wicking/liquid retention, polyethylene, shape memory foam polymers, paper, pulp, cotton, polycotton, viscose, asahi nylon, bamboo, polyacrylamide, poly(N-isopropylacrylamide), polyethylene glycol, collagen, agarose, hyaluronic acid, poly(organophosphazenes), chitosan, polyacrylic acid, polymethylmethacrylate, poly(2-(dimethylamino) ethyl methacrylate), poly(2-(diethylamino) ethyl methacrylate), and poly(2-vinylpyridine).

5. The pad of claim 1, further comprising a skin contact layer attached to one side of the open cell foam layer and comprising a non-absorbent material, to provide a barrier between skin of the perineal area and the open cell foam layer.

6. The pad of claim 5, wherein the skin contact layer comprises multiple perforations to allow flow of fluid through the skin contact layer.

7. The pad of claim 1, wherein the open cell foam layer comprises at least one opening extending through the thickness of the open cell foam layer.

8. The pad of claim 7, wherein the at least one opening comprises multiple openings selected from the group consisting of slits and perforations.

9. A method for treating a perineal area of a woman before or after childbirth, the method comprising:
applying a pad to the perineal area, wherein the pad comprises:
an open cell foam layer having a width to fit within the perineal area; and
a substance having a viscosity of at least 400 centipoise integrated with the open cell foam layer which provides a gel like consistency and allows passive diffusion of the substance through the open cell foam layer to give a uniform saturation, the substance comprising witch hazel, aloe vera, and water;
wherein the open cell foam layer has a thickness of about 1 millimeter to about 30 millimeters such that the open cell foam layer is flexible and can conform to the perineal area of the woman when hydrated and frozen; and
leaving the pad in place on the perineal area for a period of time.

10. The method of claim 9, further comprising freezing the pad before applying the pad to the perineal area.

11. The method of claim 9, further comprising cooling the pad without freezing it, before applying the pad to the perineal area.

12. The method of claim 9, further comprising heating the pad before applying it to the perineal area.

13. The method of claim 9, further comprising molding the pad to fit a shape of the perineal area.

14. The method of claim 9, further comprising applying the substance to the open cell foam layer before applying the pad to the perineal area.

15. The method of claim 9, further comprising removing the pad from a sealed package in which the substance has combined with the open cell foam layer.

16. The method of claim 9, wherein the substance is configured to serve a therapeutic purpose selected from the group consisting of pain reduction, anti-inflammatory, post-partum depression reduction, anti-constipation effects, anti-infective effects with aseptic properties, anti-itch, reduction of infection risk, swelling reduction and bleeding reduction.

17. A pad for treating a perineal area of a woman before or after childbirth, the pad comprising:
a skin contact layer;
an open cell foam layer coupled with one side of the skin contact layer; and
a substance having a viscosity of at least 400 centipoise integrated with the open cell foam layer which provides a gel like consistency and allows passive diffusion of the substance through the open cell foam layer to give a uniform saturation, the substance comprising witch hazel, aloe vera, and water;
wherein the open cell foam layer has a thickness of about 1 millimeter to about 30 millimeters such that the foam layer is flexible, and can conform to the perineal area of the woman when hydrated and frozen.

18. The pad of claim 17, wherein the substance is integrated with the open cell foam layer by a method selected from the group consisting of saturating, coating, soaking, and spraying.

19. The pad of claim 17, wherein the substance is configured to serve a therapeutic purpose selected from the group consisting of pain reduction, anti-inflammatory, post-partum depression reduction, anti-constipation effects, anti-infective effects with aseptic properties, anti-itch, reduction of infection risk, swelling reduction and bleeding reduction.

20. The pad of claim 17, wherein the open cell foam layer comprises a material selected from the group consisting of polyurethane, felt, neoprene, polyester, foam rubber, polystyrene, XPS foam, polyvinyl chloride, EVA-PE foams, silicone foams, cellulose or paper based foams or celled structures for wicking/liquid retention, polyethylene, shape memory foam polymers, paper, pulp, cotton, polycotton, viscose, asahi nylon, bamboo, polyacrylamide, poly(N-isopropylacrylamide), polyethylene glycol, collagen, agarose, hyaluronic acid, poly(organophosphazenes), chitosan, polyacrylic acid, polymethylmethacrylate, poly(2-(dimethylamino) ethyl methacrylate), poly(2-(diethylamino) ethyl methacrylate), and poly(2-vinylpyridine).

21. The pad of claim 17, wherein the skin contact layer comprises a non-absorbent material, to provide a barrier between the skin of the woman and the foam layer.

22. The pad of claim 17, wherein at least one of the skin contact layer or the open cell foam layer comprises at least one of multiple perforations or multiple slits.

23. The pad of claim 17, wherein the skin contact layer and the open cell foam layer are flexible enough when frozen to be molded to fit the perineal area.

24. A method for making a perineal pad for treating a perineal area of a woman before or after childbirth, the method comprising:
providing an open cell foam layer having a width to fit within the perineal area and a thickness of about 1 millimeter to about 30 millimeters such that the open cell foam layer is flexible and can conform to the perineal area of the woman when hydrated and frozen;
applying a substance having a viscosity of at least 400 centipoise to be integrated with the open cell foam layer which provides a gel like consistency and allows passive diffusion of the substance through the open cell foam layer to give a uniform saturation, the substance comprising witch hazel, aloe vera, and water, and allowing the substance to permeate partway into the open cell foam layer; and
sealing the open cell foam layer inside a sealed package to allow the substance to further permeate into the open cell foam layer within the sealed package over time.

25. The method of claim 24, wherein the substance is integrated with the open cell foam layer by a method selected from the group consisting of saturating, coating, soaking, and spraying.

26. The method of claim 24, wherein the substance is configured to serve a therapeutic purpose selected from the group consisting of pain reduction, anti-inflammatory, post-partum depression reduction, anti-constipation effects, anti-infective effects with aseptic properties, anti-itch, reduction of infection risk, swelling reduction and bleeding reduction.

27. The method of claim 24, wherein the open cell foam layer comprises a material selected from the group consisting of polyurethane, felt, neoprene, polyester, foam rubber, polystyrene, XPS foam, polyvinyl chloride, EVA-PE foams, silicone foams, cellulose or paper based foams or celled structures for wicking/liquid retention, polyethylene, shape memory foam polymers, paper, pulp, cotton, polycotton, viscose, asahi nylon, bamboo, polyacrylamide, poly(N-isopropylacrylamide), polyethylene glycol, collagen, agarose, hyaluronic acid, poly(organophosphazenes), chitosan, polyacrylic acid, polymethylmethacrylate, poly(2-(dimethylamino) ethyl methacrylate), poly(2-(diethylamino) ethyl methacrylate), and poly(2-vinylpyridine).

28. The method of claim 24, wherein a skin contact layer comprising a non-absorbent material provides a barrier between the skin of the woman and the open cell foam layer.

29. The method of claim 24, further comprising attaching a skin contact layer to one side of the open cell foam layer, wherein the skin contact layer comprises an impermeable material.

30. The method of claim 24, further comprising forming at least one of multiple perforations or multiple slits in the open cell foam layer.

\* \* \* \* \*